US012629511B2

(12) United States Patent
Wasserman et al.

(10) Patent No.: US 12,629,511 B2
(45) Date of Patent: May 19, 2026

(54) ELECTRODE ASSEMBLY FOR APPLYING TUMOR TREATING FIELDS (TTFIELDS) THAT INCLUDES A PLURALITY OF THERMALLY LINKED BUT ELECTRICALLY ISOLATED GRAPHITE SHEETS

(71) Applicant: Novocure GmbH, Root (CH)

(72) Inventors: Yoram Wasserman, Haifa (IL); Stas Obuchovsky, Haifa (IL); Nataliya Kuplennik, Kanata (CA); David Shapiro, Haifa (IL)

(73) Assignee: Novocure GmbH, Baar (CH)

(*) Notice: Subject to any disclaimer, the term of this patent is extended or adjusted under 35 U.S.C. 154(b) by 229 days.

(21) Appl. No.: 18/215,891

(22) Filed: Jun. 29, 2023

(65) Prior Publication Data

US 2024/0001111 A1 Jan. 4, 2024

Related U.S. Application Data

(60) Provisional application No. 63/357,111, filed on Jun. 30, 2022.

(51) Int. Cl.
*A61N 1/04* (2006.01)

(52) U.S. Cl.
CPC .................................. *A61N 1/0496* (2013.01)

(58) Field of Classification Search
None
See application file for complete search history.

(56) References Cited

U.S. PATENT DOCUMENTS

| | | | | |
|---|---|---|---|---|
| 5,678,545 | A * | 10/1997 | Stratbucker ............ | A61B 5/259 600/394 |
| 6,532,379 | B2 * | 3/2003 | Stratbucker .......... | A61N 1/0492 600/382 |
| 6,868,289 | B2 | 3/2005 | Palti | |
| 7,016,725 | B2 | 3/2006 | Palti | |

(Continued)

FOREIGN PATENT DOCUMENTS

EP 3988024 A1 4/2022

OTHER PUBLICATIONS

International Search Report and Written Opinion issued in application PCT/IB2023/056720 dated Nov. 21, 2023.

(Continued)

*Primary Examiner* — Mallika D Fairchild
(74) *Attorney, Agent, or Firm* — Potomac Law Group, PLLC

(57) ABSTRACT

Alternating electric fields (e.g., TTFields) may be applied to a subject's body using electrode assemblies, each of which includes a plurality of graphite sheets (or sheets of another conductive anisotropic material) that are positioned adjacent to, but not touching, each other. One or more electrode elements are disposed in electrical contact with each of the graphite sheets. Strips of electrically insulating and thermally conductive material are disposed between the graphite sheets, and these strips are positioned in thermal contact with the adjacent graphite sheets. The graphite sheets facilitate the passive spreading of heat within the confines of any given sheet. And the strips of material allow the passive spreading of heat to continue beyond the confines of any given sheet without compromising inter-sheet electrical isolation.

20 Claims, 7 Drawing Sheets

(56) References Cited

U.S. PATENT DOCUMENTS 7,089,054 B2 8/2006 Palti
7,136,699 B2 11/2006 Palti
7,333,852 B2 2/2008 Palti
7,467,011 B2 12/2008 Palti
7,519,420 B2 4/2009 Palti
7,565,205 B2 7/2009 Palti
7,565,206 B2 7/2009 Palti
7,599,745 B2 10/2009 Palti
7,599,746 B2 10/2009 Palti
7,706,890 B2 4/2010 Palti
7,715,921 B2 5/2010 Palti
7,805,201 B2 9/2010 Palti
7,890,183 B2 2/2011 Palti et al.
7,912,540 B2 3/2011 Palti
7,917,227 B2 3/2011 Palti
8,019,414 B2 9/2011 Palti
8,027,738 B2 9/2011 Palti
8,170,684 B2 5/2012 Palti
8,175,698 B2 5/2012 Palti et al.
8,229,555 B2 7/2012 Palti
RE43,618 E 8/2012 Palti
8,244,345 B2 8/2012 Palti
8,406,870 B2 3/2013 Palti
8,447,395 B2 5/2013 Palti et al.
8,447,396 B2 5/2013 Palti et al.
8,465,533 B2 6/2013 Palti
8,706,261 B2 4/2014 Palti
8,715,203 B2 5/2014 Palti
8,718,756 B2 5/2014 Palti
8,764,675 B2 7/2014 Palti
9,023,090 B2 5/2015 Palti
9,023,091 B2 5/2015 Palti
9,039,674 B2 5/2015 Palti et al.
9,056,203 B2 6/2015 Palti et al.
9,440,068 B2 9/2016 Palti et al.
9,655,669 B2 5/2017 Palti et al.
9,750,934 B2 9/2017 Palti et al.
9,910,453 B2 3/2018 Wasserman et al.
10,188,851 B2 1/2019 Wenger et al.
10,441,776 B2 10/2019 Kirson et al.
10,779,875 B2 9/2020 Palti et al.
10,967,167 B2 4/2021 Hagemann et al.
11,103,698 B2 8/2021 Chang et al.
11,191,956 B2 12/2021 Giladi et al.
2004/0176804 A1 9/2004 Palti
2005/0209642 A1 9/2005 Palti
2006/0167499 A1 7/2006 Palti
2006/0276858 A1* 12/2006 Palti .................... A61N 1/0408 607/76
2007/0225766 A1 9/2007 Palti
2007/0239213 A1 10/2007 Palti
2009/0076366 A1 3/2009 Palti
2012/0029419 A1 2/2012 Palti
2012/0283726 A1 11/2012 Palti
2014/0221807 A1 8/2014 Park et al.
2014/0330268 A1 11/2014 Palti et al.
2017/0120041 A1 5/2017 Wenger et al.
2017/0215939 A1 8/2017 Palti et al.
2017/0281934 A1 10/2017 Giladi et al.
2018/0001075 A1 1/2018 Kirson et al.
2018/0008708 A1 1/2018 Giladi et al.
2018/0050200 A1* 2/2018 Wasserman .......... A61N 1/0408
2018/0160933 A1 6/2018 Urman et al.
2018/0202991 A1 7/2018 Giladi et al.
2018/0280687 A1 10/2018 Carter et al.
2019/0117956 A1 4/2019 Wenger et al.
2019/0117963 A1 4/2019 Travers et al.
2019/0117970 A1 4/2019 Schmidt et al.
2019/0224474 A1 7/2019 Yang et al.
2019/0308016 A1 10/2019 Wenger et al.
2020/0001069 A1 1/2020 Kirson et al.
2020/0009376 A1 1/2020 Chang et al.
2020/0009377 A1 1/2020 Chang et al.
2020/0016067 A1 1/2020 Gotlib et al.
2020/0023179 A1 1/2020 Bomzon et al.
2020/0061360 A1 2/2020 Hagemann et al.
2020/0061361 A1 2/2020 Hagemann et al.
2020/0069937 A1 3/2020 Naveh et al.
2020/0078582 A1 3/2020 Alon et al.
2020/0108031 A1 4/2020 Borst et al.
2020/0114141 A1 4/2020 Bomzon et al.
2020/0114142 A1 4/2020 Bomzon et al.
2020/0121728 A1 4/2020 Wardak et al.
2020/0129761 A1 4/2020 Bomzon et al.
2020/0146586 A1 5/2020 Naveh et al.
2020/0155835 A1 5/2020 Wasserman et al.
2020/0171297 A1 6/2020 Kirson et al.
2020/0179512 A1 6/2020 Giladi et al.
2020/0219261 A1 7/2020 Shamir et al.
2020/0269037 A1 8/2020 Hagemann et al.
2020/0269041 A1 8/2020 Zeevi et al.
2020/0269042 A1 8/2020 Giladi et al.
2020/0368525 A1 11/2020 Maag et al.
2021/0031031 A1 2/2021 Wasserman et al.
2021/0038584 A1 2/2021 Voloshin-Sela
2021/0060334 A1 3/2021 Avraham et al.
2021/0069503 A1 3/2021 Tran et al.
2021/0138233 A1 5/2021 Deslauriers
2021/0162228 A1 6/2021 Urman et al.
2021/0177492 A1 6/2021 Travers et al.
2021/0187277 A1 6/2021 Wasserman et al.
2021/0196348 A1 7/2021 Wasserman
2021/0199640 A1 7/2021 Patel et al.
2021/0203250 A1 7/2021 Wasserman
2021/0268247 A1 9/2021 Story et al.
2021/0299439 A1 9/2021 Shamir et al.
2021/0299440 A1 9/2021 Deslauriers et al.
2021/0308446 A1 10/2021 Alon et al.
2021/0330950 A1 10/2021 Hagemann et al.
2021/0346694 A1 11/2021 Wasserman et al.
2021/0379362 A1 12/2021 Smith et al.
2021/0408383 A1 12/2021 Kalra et al.
2022/0088403 A1 3/2022 Voloshin-Sela et al.
2022/0095997 A1 3/2022 Wasserman
2022/0096821 A1 3/2022 Kirson et al.
2022/0096829 A1 3/2022 Farber et al.
2022/0118249 A1 4/2022 Bomzon et al.
2022/0148171 A1 5/2022 Marciano et al.
2022/0161028 A1 5/2022 Giladi et al.
2022/0193435 A1 6/2022 Wasserman et al.
2022/0267445 A1 8/2022 Tran et al.
2022/0280787 A1 9/2022 Bomzon et al.
2022/0288395 A1 9/2022 Voloshin-Sela et al.
2022/0313992 A1 10/2022 Wasserman
2022/0323753 A1 10/2022 Voloshin-Sela et al.
2022/0387784 A1 12/2022 Kirson et al.
2022/0395699 A1 12/2022 Doyle
2022/0409893 A1 12/2022 Wasserman et al.
2023/0000384 A1 1/2023 Wasserman et al.
2023/0001197 A1 1/2023 Wasserman et al.
2023/0001221 A1 1/2023 Farber
2023/0009366 A1 1/2023 Voloshin-Sela et al.
2023/0019638 A1 1/2023 Wasserman
2023/0037806 A1 2/2023 Wasserman et al.
2023/0043071 A1 2/2023 Wasserman et al.
2023/0098801 A1 3/2023 Carlson
2023/0141087 A1 5/2023 Giladi et al.
2023/0149708 A1 5/2023 O'Connell et al.
2023/0168242 A1 6/2023 Sarkisian et al.
2023/0188055 A1 6/2023 Wasserman
2023/0191123 A1 6/2023 Wasserman et al.
2023/0201616 A1 6/2023 Carlson
2023/0218912 A1 7/2023 Giladi et al.
2023/0241374 A1 8/2023 Shnaiderman et al.
2023/0248826 A1 8/2023 Giladi et al.
2023/0248969 A1 8/2023 Wasserman et al.
2023/0310848 A1 10/2023 Voloshin-Sela et al.
2023/0310849 A1 10/2023 Wasserman et al.
2023/0310877 A1 10/2023 Giladi

(56) References Cited

OTHER PUBLICATIONS

Partial International Search Report and Written Opinion issued in application No. PCT/IB2023/056720 dated Oct. 5, 2023.

* cited by examiner

PRIOR ART

ELECTRODE ASSEMBLY FOR APPLYING TUMOR TREATING FIELDS (TTFIELDS) THAT INCLUDES A PLURALITY OF THERMALLY LINKED BUT ELECTRICALLY ISOLATED GRAPHITE SHEETS

CROSS REFERENCE TO RELATED APPLICATIONS

This application claims the benefit of U.S. Provisional Application 63/357,111, filed Jun. 30, 2022, which is incorporated herein by reference in its entirety.

BACKGROUND

Tumor Treating Fields (TTFields) therapy is a proven approach for treating tumors using alternating electric fields at frequencies e.g., between 50 kHz-1 MHz, more commonly 100-500 KHz. The alternating electric fields are induced by electrode assemblies (e.g., arrays of capacitively coupled electrodes, also called transducer arrays) placed on opposite sides of the subject's body. When an AC voltage is applied between opposing electrode assemblies, an AC current is coupled through the electrode assemblies and into the subject's body. And higher currents are strongly correlated with higher efficacy of treatment.

FIG. 1A is a schematic representation of a prior art electrode assembly 40 including nine prior art electrode elements, labeled X1-X9. FIG. 1B is a cross sectional schematic view of electrode elements X1-X3 of the electrode assembly 40, taken along the dashed line in FIG. 1A.

As shown in FIG. 1B, electrode element X1 (taken as exemplary) includes a metal layer (shown with diagonal hatching) and a ceramic (dielectric) layer. A respective layer of electrically conductive hydrogel is provided between each ceramic layer and the subject's skin, to ensure good electrical contact of the electrode elements with the body. An AC voltage from an AC voltage generator (not shown) is applied to the metal layers of electrode elements in opposing electrode assemblies to generate the TTFields in the subject's body.

During use, the hydrogel and the skin under the electrode elements heat up, and safety considerations require that the skin temperature remains below a safety threshold (e.g., 41° C.). Because the vast majority of the heat appears immediately below the electrode elements X1-X9, the prior art electrode assembly has hot spots immediately below the electrode elements, and cooler regions positioned between the electrode elements. And those hot spots limit the amount of current that can be delivered through the prior art electrode assemblies.

SUMMARY OF THE INVENTION

One aspect of this application is directed to a first electrode assembly that comprises a first sheet of a conductive anisotropic material having a front side and a front surface and a rear side and a rear surface, and one or more first electrode elements, each of which is disposed in electrical contact with the first sheet. The first electrode assembly also comprises a second sheet of conductive anisotropic material having a front side and a front surface and a rear side and a rear surface, and one or more second electrode elements, each of which is disposed in electrical contact with the second sheet. The second sheet is positioned adjacent to the first sheet without touching the first sheet. The first electrode assembly also comprises a first strip of electrically insulating and thermally conductive material disposed between the first sheet and the second sheet. The first strip of material is positioned in thermal contact with both the first sheet and the second sheet.

In some embodiments of the first electrode assembly, the first strip of material comprises coated graphite. In some embodiments of the first electrode assembly, the first strip of material is less than 2 mm wide. In some embodiments of the first electrode assembly, the first and second sheets each comprise a sheet of synthetic graphite, pyrolytic graphite, graphitized polymer film, or graphite foil made from compressed high purity exfoliated mineral graphite.

Some embodiments of the first electrode assembly further comprise a first layer of skin-compatible conductive material disposed on the front side of the first sheet, and a second layer of skin-compatible conductive material disposed on the front side of the second sheet.

In some embodiments of the first electrode assembly, there are at least two first electrode elements and at least two second electrode elements. Each of the first electrode elements comprises a respective first metal layer and a respective first dielectric layer disposed on the respective first metal layer, and each of the first dielectric layers is disposed in electrical contact with and located behind the first sheet. Each of the second electrode elements comprises a respective second metal layer and a respective second dielectric layer disposed on the respective second metal layer, and each of the second dielectric layers is disposed in electrical contact with and located behind the second sheet.

Optionally, in the embodiments of the previous paragraph, each of the first dielectric layers and each of the second dielectric layers comprises a polymer layer having a dielectric constant of at least 10. Optionally, in the embodiments of the previous paragraph, the electrical contact between each of the first dielectric layers and the first sheet is implemented using a first layer of conductive gel or conductive adhesive, and the electrical contact between each of the second dielectric layers and the second sheet is implemented using a second layer of conductive gel or conductive adhesive.

In some embodiments of the first electrode assembly, there are at least two first electrode elements and at least two second electrode elements. Each of the first electrode elements comprises a respective first metal layer disposed in electrical contact with the first sheet, and each of the second electrode elements comprises a respective second metal layer disposed in electrical contact with the second sheet.

In some embodiments of the first electrode assembly, there are at least two first electrode elements and at least two second electrode elements and the electrode assembly further comprises a plurality of first metal conductors, each of which is disposed in electrical contact with only a single respective one of the first electrode elements; and a plurality of second metal conductors, each of which is disposed in electrical contact with only a single respective one of the second electrode elements.

In some embodiments of the first electrode assembly, there are at least two first electrode elements and at least two second electrode elements and the electrode assembly further comprises at least one first metal conductor arranged to electrically connect all of the first electrode elements; and at least one second metal conductor arranged to electrically connect all of the second electrode elements.

Some embodiments of the first electrode assembly further comprise a support having an adhesive backing shaped and dimensioned to hold the electrode assembly against a person's body with the front side of the first sheet and the front side of the second sheet facing the person's body.

Some embodiments of the first electrode assembly further comprise a coil, and energy from a main conductor power source is diverted by the coil and stored locally on a capacitor for reuse in powering a controller, or a circuit, or a means to generate digital data related to temperature measurements.

In some embodiments of the first electrode assembly, there are at least two first electrode elements and at least two second electrode elements and the electrode assembly further comprises a third sheet of a conductive anisotropic material having a front side and a front surface and a rear side and a rear surface; a plurality of third electrode elements, each of which is disposed in electrical contact with the third sheet; and a second strip of electrically insulating and thermally conductive material disposed between the second sheet and the third sheet. The third sheet is positioned adjacent to the second sheet without touching the second sheet and without touching the first sheet, and the second strip of material is positioned in thermal contact with both the second sheet and the third sheet.

Optionally, the embodiments of the previous paragraph may further comprise a plurality of first metal conductors, each of which is disposed in electrical contact with only a single respective one of the first electrode elements; a plurality of second metal conductors, each of which is disposed in electrical contact with only a single respective one of the second electrode elements; and a plurality of third metal conductors, each of which is disposed in electrical contact with only a single respective one of the third electrode elements.

In some embodiments of the first electrode assembly, there are at least two first electrode elements and at least two second electrode elements and the electrode assembly further comprises a third sheet of a conductive anisotropic material having a front surface and a rear surface; a plurality of third electrode elements, each of which is disposed in electrical contact with the third sheet; a second strip of electrically insulating and thermally conductive material disposed between the second sheet and the third sheet; a first layer of skin-compatible conductive material disposed on the front side of the first sheet; a second layer of skin-compatible conductive material disposed on the front side of the second sheet; and a third layer of skin-compatible conductive material disposed on the front side of the third sheet. The third sheet is positioned adjacent to the second sheet without touching the second sheet and without touching the first sheet, and the second strip of material is positioned in thermal contact with both the second sheet and the third sheet. In these embodiments, the first and second strips of material each comprises coated graphite.

Another aspect of this application is directed to a second electrode assembly that comprises a first sheet of a conductive anisotropic material; at least one first electrode element disposed in electrical contact with the first sheet; a second sheet of a conductive anisotropic material positioned adjacent to the first sheet without touching the first sheet; at least one second electrode element disposed in electrical contact with the second sheet; and a strip of electrically insulating and thermally conductive material disposed between the first sheet and the second sheet. The strip of material is positioned in thermal contact with both the first sheet and the second sheet.

In some embodiments of the second electrode assembly, the strip of material comprises coated graphite. In some embodiments of the second electrode assembly, the strip of material is less than 2 mm Wide. In some embodiments of the second electrode assembly, the first and second sheets each comprises a sheet of synthetic graphite, pyrolytic graphite, graphitized polymer film, or graphite foil made from compressed high purity exfoliated mineral graphite.

Another aspect of this application is directed to a first method of planning treatment of a target region in a subject's body using alternating electric fields. The first method comprises positioning a first set of N electrode elements on or in the subject's body on a first side of the target region. Each of the N electrode elements is disposed in electrical contact with a respective sheet of a conductive anisotropic material, and N is at least 4. The first method also comprises positioning a second set of M electrode elements on or in the subject's body on a second side of the target region. Each of the M electrode elements is disposed in electrical contact with a respective sheet of a conductive anisotropic material, and M is at least 4. The second side is opposite to the first side. The first method also comprises sequentially measuring, during a first window of time, a respective impedance or conductance between each of the N electrode elements in the first set and each of the M electrode elements in the second set; calculating, based on the impedance or conductance measurements, a first impedance or conductance at each of at least 27 voxels that correspond to locations between the first set of N electrode elements and the second set of M electrode elements; and generating a plan, based on the first impedances or conductances of the voxels, for treating the target region with alternating electric fields.

In some instances of the first method, a plurality of strips of electrically insulating and thermally conductive material are disposed between adjacent sheets of the conductive anisotropic material, and each of the strips is positioned in thermal contact with the adjacent sheets. In some instances of the first method, each of the sheets of the conductive anisotropic material comprises synthetic graphite, pyrolytic graphite, graphitized polymer film, or graphite foil made from compressed high purity exfoliated mineral graphite. In some instances of the first method, the plan comprises generating a recommendation to move at least one set of electrode elements to a different position on or in the subject's body.

Some instances of the first method further comprise, subsequent to the step of generating the plan, applying an alternating voltage between a plurality of the electrode elements in the first set and a plurality of the electrode elements in the second set in order to induce an electric field in the target region.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figures 1A, 1B:
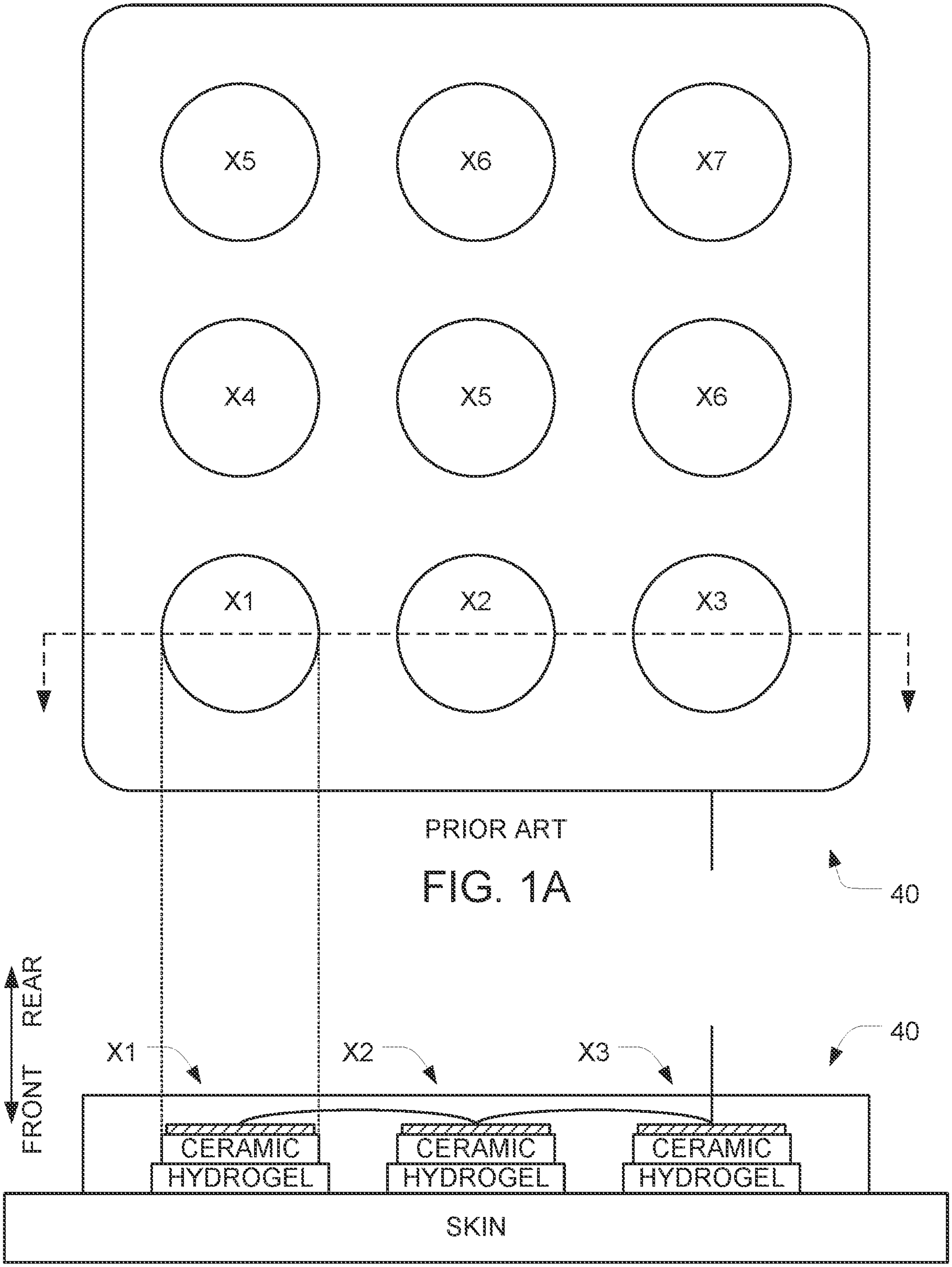
FIG. 1A is a schematic representation of a prior art electrode assembly.
FIG. 1B is a cross sectional view of the FIG. 1A prior art electrode assembly.

This application describes exemplary electrode assemblies that may be used, e.g., for delivering alternating electric fields to a subject's body. The alternating electric fields could be tumor treating fields (TTFields) for treating one or more cancers or tumors located in the subject's body, and most of the examples below assume that context. But the electrode assemblies described herein may also be used for delivering other electrical signals, including alternating electric fields that are applied for purposes other than treating tumors. For example, the electrode assemblies described herein may be used to apply alternating electric fields for increasing the permeability of the blood brain barrier (e.g., as described in U.S. Pat. No. 10,967,167), or for increasing the permeability of cell membranes (e.g., as described in U.S. Pat. No. 11,103,698).

When TTFields are applied to a subject's body, the temperature at the subject's body may increase in response to increases in the induced electric field strength. Regulations limit the amount of current that can be driven through an electrode assembly to an amount that keeps the measured temperature at locations on the subject's body below a temperature threshold. As practiced in the art, the temperature at the location of the electrode assemblies on the subject's body is controlled to be below the temperature threshold by reducing the operational current driven by the electrode assemblies, which will reduce the strength of the resulting TTFields. This in turn becomes an over-riding limitation on the TTFields strength that can be used to treat the tumor.

On electrode assemblies that comprise multiple electrode elements, the portions of the electrode assemblies positioned directly beneath the electrode elements get hotter than the portions of the electrode assemblies positioned between the electrode elements. Furthermore, on electrode assemblies that comprise multiple electrode elements, higher currents flow through the electrode elements located along the edge of the array compared to the electrode elements located toward the middle of the array. Further still, an electrode element located at a corner or similar sharp bend in the edge of the array will have a higher current than other electrode elements along the edge and near the center of the array. The tendency of an electrode assembly to drive higher currents through electrode elements located along the edge of the array, and particularly at the corners, is referred to herein as the "edge effect."

An uneven distribution of current through the electrode assembly due to either the distribution of the electrode elements or the edge effect can lead to higher temperature zones (or "hot spots") e.g., at the corners or edges of the electrode assembly. These hot spots are the locations that reach the threshold temperature first and therefore control the requirement to reduce the current. As such, the generation of hot spots limits the maximum operational current that may be driven by an electrode assembly, and the strength of the resulting TTFields.

This application describes a variety of approaches for reducing or minimizing the uneven distribution of current in electrode assemblies, which ultimately permits the use of higher operating currents without exceeding the threshold temperature. Electrode assemblies operated with increased current can induce stronger TTFields in the subject's body, ultimately leading to better patient outcomes. The electrode assemblies disclosed herein allow current and heat to be spread more evenly over the array thereby minimizing or eliminating hot spots.

The approaches described below in connection with FIGS. 2A/B and 4-8 reduce or minimize hotspots on electrode assemblies using sheets of a conductive anisotropic material (e.g., sheets of pyrolytic graphite) that are incorporated into the electrode assembly to passively carry heat away from the hot spots, as described below. This lowers the temperature of the hot spots and raises the temperature of the cooler regions when a given AC voltage is applied to the electrode assembly (as compared to the FIG. 1A/B prior art configuration described above). Accordingly, the current can be increased (thereby increasing the therapeutic effect) without exceeding the safety temperature threshold at any point on the subject's skin.

Figure 2A:
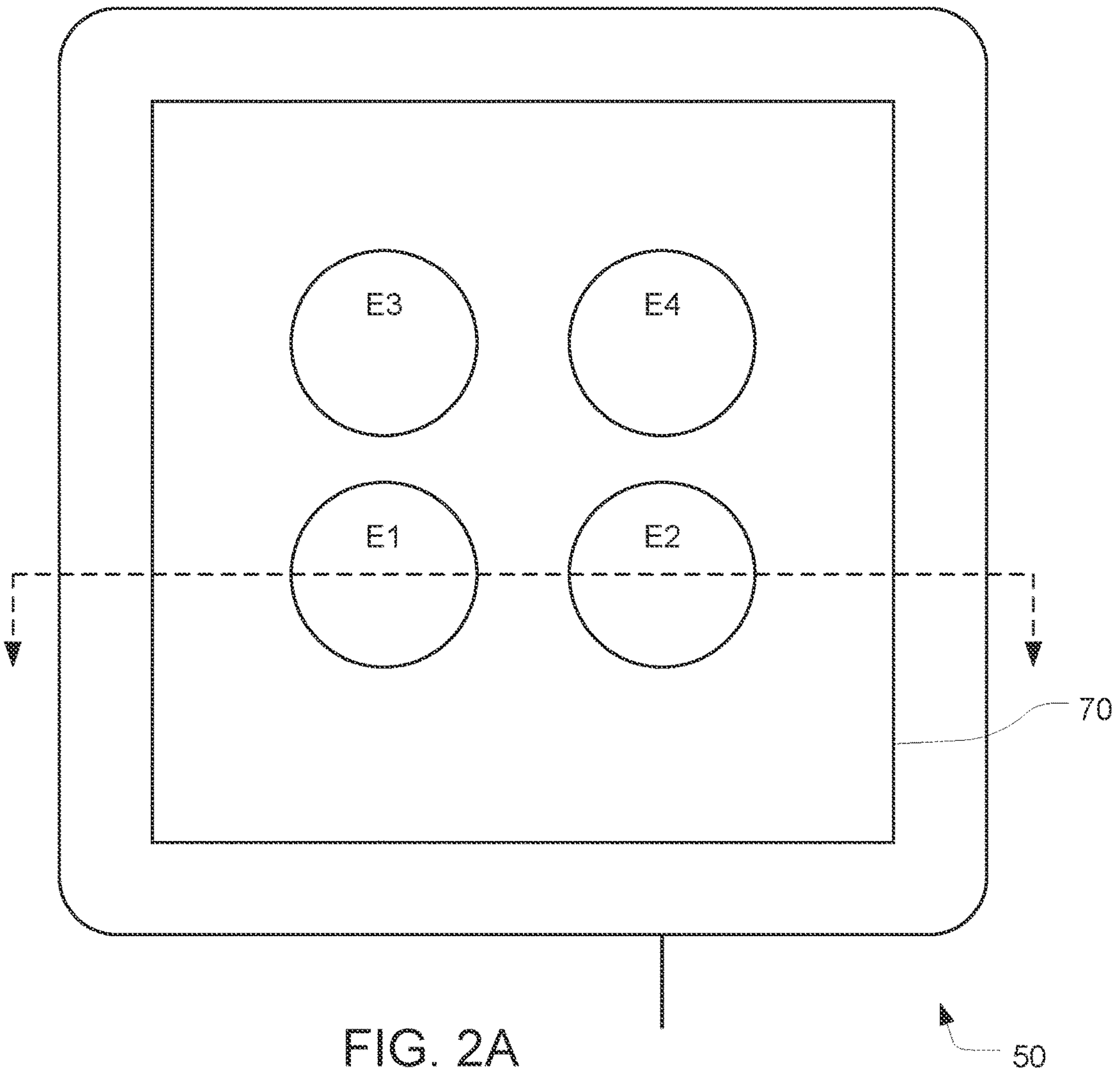
FIG. 2A is a plan view of an electrode assembly that is used for applying TTFields to a subject's body.
Figure 2B:
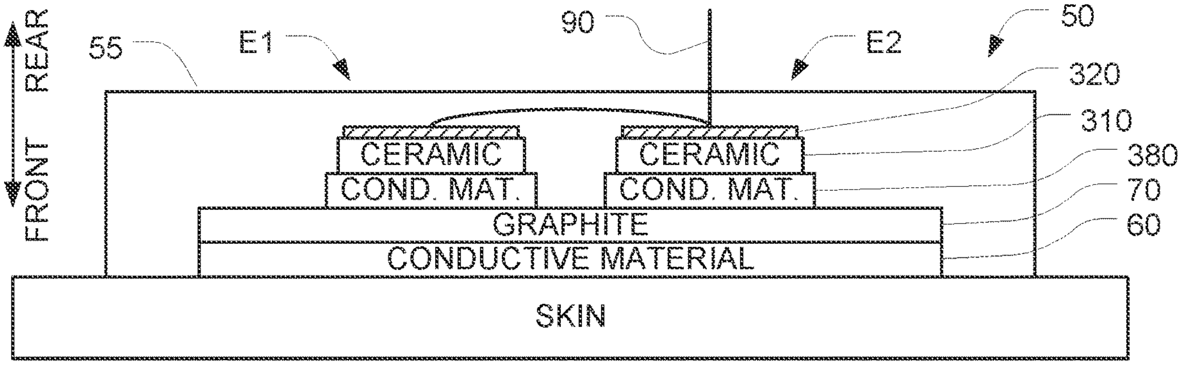
FIG. 2B is a cross sectional view of the FIG. 2A electrode assembly.

FIG. 2A is a schematic representation of an electrode assembly 50 of an embodiment including electrode elements used for applying TTFields to a subject's body, and FIG. 2B is a cross sectional view of the same electrode assembly 50, taken along the dashed line in FIG. 2A. In FIG. 2A, only four electrode elements labeled E1-E4 are shown, but additional electrode elements may be included in the electrode assembly 50. In alternative embodiments, the electrode assembly 50 includes only a single electrode element.

The electrode assembly 50 includes a sheet of conductive anisotropic material (e.g., a sheet of graphite) 70 having a front side and a front surface (facing towards the subject's skin in FIG. 2B) and a rear side and a rear surface. Examples of suitable forms of graphite include synthetic graphite, such as pyrolytic graphite (including but not limited to Pyrolytic Graphite Sheet (PGS), available from Panasonic Industry, Kadoma, Osaka, Japan), another form of graphite including but not limited to graphite foil made from compressed high purity exfoliated mineral graphite (including but not limited to MinGraph® 2010A Flexible Graphite, available from Mineral Seal Corp., Tucson, Arizona, USA), or graphitized polymer film, e.g., graphitized polyimide film, (including but not limited to Kaneka Corp., Moka, Tochigi, Japan). Note that in the examples described herein and in the figures, the sheets of conductive anisotropic material are described and depicted as sheets of graphite. But in alternative embodiments, conductive anisotropic materials other than graphite may be used instead of graphite.

Exemplary embodiments disclosed herein incorporate into the electrode assembly a sheet of material having anisotropic thermal properties and/or anisotropic electrical properties (referred to herein also as a sheet of conductive anisotropic material). If the sheet of material has anisotropic thermal properties (e.g., greater in-plane thermal conductivity than perpendicular to the plane), then the sheet spreads the heat out more evenly over a larger surface area. If the sheet of material has anisotropic electrical properties (e.g., greater in-plane electrical conductivity than perpendicular to the plane; or, conversely, lower in-plane resistance than perpendicular to the plane), then the sheet spreads the current out more evenly over a larger surface area. In each case, this lowers the temperature of the hot spots and raises the temperature of the cooler regions when a given AC voltage is applied to the apparatus. Accordingly, the current can be increased (thereby increasing the therapeutic effect) without exceeding the safety temperature threshold at any point on the subject's skin.

In some embodiments, the anisotropic material is anisotropic with respect to electrical conductivity properties. In some embodiments, the anisotropic material is anisotropic with respect to thermal conductivity properties. In some embodiments, the anisotropic material is anisotropic with respect to both electrical conductivity properties and thermal conductivity properties.

The anisotropic thermal properties include directional thermal properties. Specifically, the sheet of anisotropic material has a first thermal conductivity in a direction that is perpendicular to its front surface. And the thermal conductivity of the sheet in directions parallel to the front surface is more than two times higher than the first thermal conductivity. In some preferred embodiments, the thermal conductivity in the parallel directions is more than ten times higher than the first thermal conductivity. For example, the thermal conductivity of the sheet in directions that are parallel to the front surface may be more than: 1.5 times, 2 times, 3 times, 5 times, 10 times, 20 times, 100 times, 200 times, or even more than 1,000 times higher than the first conductivity.

The anisotropic electrical properties include directional electrical properties. Specifically, the sheet of anisotropic material has a first resistance in a direction that is perpendicular to its front surface. And resistance of the sheet in directions parallel to the front surface is less than the first resistance. In some preferred embodiments, the resistance in the parallel directions is less than half of the first resistance or less than 10% of the first resistance. For example, the resistance of the sheet 70 in directions that are parallel to the front surface may be less than: 75%, 50%, 40%, 30%, 20%, 10%, 5%, 1%, 0.5%, or even less than 0.1% of the first resistance.

In some embodiments (e.g., when the sheet of anisotropic material is a sheet of pyrolytic graphite), the sheet of anisotropic material has both anisotropic electrical properties and anisotropic thermal properties. Preferably, the anisotropic material is nonmetallic.

The electrode assembly 50 further includes a front layer of biocompatible conductive material 60 disposed on the front side (e.g., on the front surface) of the sheet of graphite 70. The front layer of material 60 is configured to ensure good electrical contact between the device and the body. In some embodiments, the front layer of material 60 covers the entire front surface of the sheet of graphite 70. The front layer of material 60 may be the same size or larger than the sheet of graphite 70. In some embodiments, the front layer of conductive material 60 comprises hydrogel. In these embodiments, the hydrogel may have a thickness between 50 and 2000 μm, such as, from 100 to 1000 μm, or even 300 to 500 μm. In some embodiments, the front layer of conductive material 60 is a non-hydrogel biocompatible conductive adhesive. In some embodiments, the front layer of conductive material 60 is a non-hydrogel biocompatible conductive adhesive such as the developmental product FLX068983—FLEXcon® OMNI-WAVE™ TT 200 BLACK H-502 150 POLY H-9 44PP-8 from FLEXcon, Spencer, MA, USA, or other such OMNI-WAVE products from FLEXcon; or ARcare® 8006 electrically conductive adhesive composition manufactured and sold by Adhesives Research, Inc. (Glen Rock, PA, USA). Non-hydrogel conductive adhesives may comprise a waterless polymer with adhesive properties with a conductive filler disposed therein (e.g., carbon particles, powder, fibers, flakes or nanotubes). The adhesive polymer may be, for example, an acrylic polymer or a silicone polymer, or combination thereof, which may be available as acrylic- or silicone-based carbon-filled adhesive tapes (e.g., a transfer tape). The adhesive may additionally include one or more conductive polymers (for example, polyaniline (PANT) or poly(3,4-ethylenedioxythiophene (PEDOT), or others known in the art). When present, the conductive filler in the front layer of conductive material 60 should be non-metallic. In these embodiments, the biocompatible conductive adhesive may have a thickness between 10 and 2,000 μm, such as, from 20 to 1000 μm, or even 30 to 400 μm.

The electrode assembly 50 further includes electrode elements E1-E4 positioned behind the sheet of graphite 70. Each electrode element E1-E4 has a front face disposed in electrical contact with the rear surface of the sheet of graphite 70. Each electrode element E1-E4 includes a layer of dielectric material 310 having a front face and a rear face, and a layer of metal 320 disposed on the rear face of the layer of dielectric material 310. The front face of the layer of dielectric material 310 is the front face of the electrode element E1-E4. The dielectric material 310 in these embodiments could be, for example, a flat piece of ceramic material with a high dielectric constant (as depicted in FIG. 2A/B), or a polymer layer that has a dielectric constant of at least 10.

In some embodiments, the layer of dielectric material 310 can have a dielectric constant ranging from 10 to 50,000. In some embodiments, the layer of dielectric material 310 comprises a high dielectric polymer material such as poly (vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CTFE)" and "Poly(VDF-TrFE-CFE)," respectively. These embodiments are particularly advantageous because the dielectric constant of these materials is on the order of 40. In some embodiments, the polymer layer can be poly(vinylidene fluoride-trifluoroethylene-chlorotrifluoroethylene-chlorofluoroethylene) or "Poly(VDF-TrFE-CTFE-CFE)."

In some embodiments, the layer of dielectric material 310 comprises a terpolymer comprising polymerized units of monomers such as VDF, TrFE, CFE and/or CTFE in any suitable molar ratio. Suitable terpolymers include those, for example, having 30 to 80 mol % VDF, 5 to 60 mol % TrFE, with CFE and/or CTFE constituting the balance of the mol % of the terpolymer.

The electrode assembly 50 further includes layers of conductive material 380 positioned between the front face of the electrode elements E1-E4 (i.e., the front faces of the layer of dielectric material 310) and the rear surface of the sheet of graphite 70. These layers of conductive material 380 facilitate the electrical contact between the front faces of the electrode elements E1-E4 and the rear surface of the sheet of graphite 70. In some embodiments, the layers of conductive material 380 are layers of hydrogel. But in alternative embodiments, a different conductive material (e.g., conductive grease, conductive adhesive, conductive tape, conductive composite, etc.) could be used. In some embodiments, the layers of conductive material 380 may be a non-hydrogel conductive adhesive, such as described above. In alternative embodiments (not shown), instead of having an individual layer of conductive material 380 positioned between the front face of each individual electrode element E1-E4 and the rear surface of the sheet of graphite 70, a single large layer of conductive material may be positioned between all of the electrode elements E1-E4 and the rear surface of the sheet of graphite 70.

The metal layers 320 of all of the electrode elements (i.e., E1-E4 in the illustrated embodiment), may be wired together (e.g., using wires, traces on a flex circuit, etc.) to a lead 90. The lead 90 supplies an AC voltage from an AC voltage generator (not shown) to the electrode elements to generate the TTFields when the electrode assembly 50 is affixed to the subject's body for treatment.

Optionally, the apparatus may include a coil, and energy from the main conductor power source may be diverted by the coil and stored locally on a capacitor for reuse in powering the controller (which may, for example, control the duty cycle), or for reuse in powering a circuit (such as for switching), or the means to generate the digital data related to temperature measurements.

Optionally, the electrode assembly 50 includes a flexible self-adhesive backing 55 configured to support the sheet of graphite 70, the electrode elements E1-E4, and the front layer of conductive material 60 so that the front layer of conductive material 60 can be positioned against the subject's skin.

As noted above, FIG. 2A is a plan schematic representation of an electrode assembly 50 including electrode elements E1-E4. When an AC voltage is applied to the electrode elements E1-E4, the current and the heat will be spread out by the sheet of graphite 70, which minimizes or eliminates hot spots. Because the current and heat in this embodiment are both spread out over a larger area, hotspots are eliminated (or at least minimized). This means that for a given applied AC voltage, the hottest point beneath the electrode assembly in the FIG. 2A/B embodiment will have a lower temperature than the hottest point beneath the electrode assembly in the FIG. 1 prior art example. Accordingly, the current can be increased (with respect to the prior art current) without exceeding the safety temperature threshold at any point beneath the electrode assembly. And this increase in current will advantageously increase the efficacy of the TTFields treatment.

The embodiments described above in connection with FIG. 2A/B make a very significant contribution to reducing the temperature of the hottest spot of any given electrode assembly by using a single sheet of graphite to passively convey heat away from the hottest spots on the electrode assembly towards cooler spots on the electrode assembly. And this passive heat transfer advantageously allows the electrode assembly to carry a higher current without exceeding the safety temperature threshold at any point on the electrode assembly.

But in certain anatomic situations, the passive heat distribution techniques described in connection with FIG. 2A/B may not carry enough heat away from the hottest spots on the electrode assembly. When this occurs, the hottest spots on the electrode assemblies still limit the amount of current that can be delivered through any given electrode assembly (because any further increases in current will cause those hottest spots to exceed the safety temperature threshold.)

Figure 3:
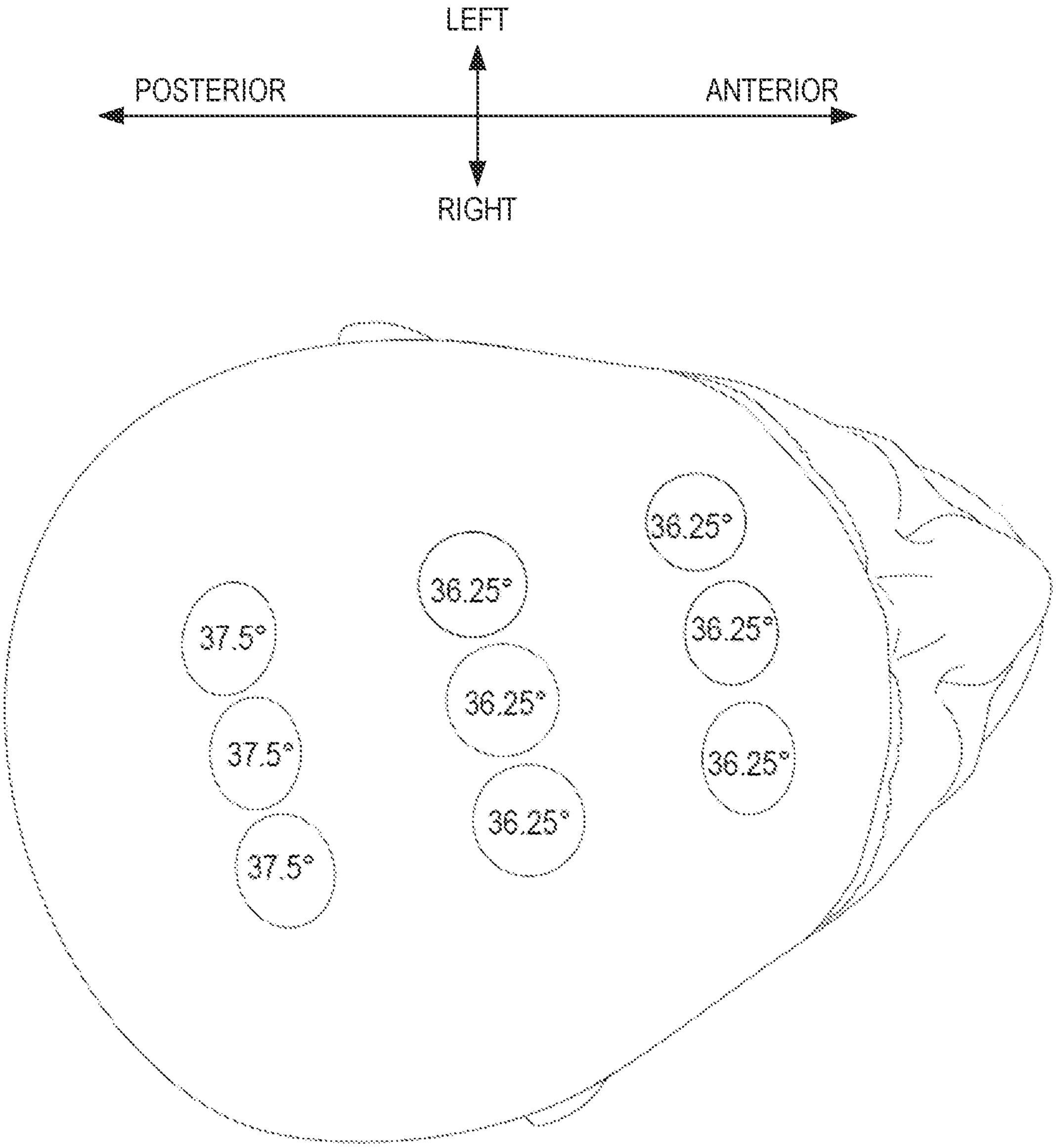
FIG. 3 is a schematic representation of a heat map of an electrode assembly that is being used in a particular anatomic situation.

One example of such an anatomic situation is when TTFields are applied between a 9-element electrode assembly positioned on the front/top of a subject's head (referred to herein as the anterior array) and a second 9-element electrode assembly is positioned on the back of a subject's head (referred to herein as the posterior array). In this anatomic situation, if the same signal is applied to all 9 electrode elements in the FIG. 1A/1B array, the rear-most three elements of the anterior array and the upper three elements of the posterior array will typically run significantly hotter than the remaining elements on those arrays, as depicted in FIG. 3 (which is a schematic representation of a heat map of the anterior array in this situation). More specifically, in the FIG. 3 example, the rear-most three elements of the anterior array are operating at about 37.5° C., while the other six elements are operating at about 36.25° C. And in this anatomic situation, the passive heat distribution techniques described in connection with FIG. 2A/B may not carry enough heat away from the hottest spots on the electrode assembly.

One potential approach to even out the temperatures of the electrode elements on an electrode assembly is to redesign the electrode assembly so that each individual electrode element can be activated independently using an independent wire (e.g., using nine wires for an electrode assembly that includes nine electrode elements). This approach is referred to herein as the "independent element approach."

Another potential approach to even out the temperatures of the electrode elements is to wire up the electrode elements in groups so that each group can be activated independently from the other groups. For example, the electrode elements in the nine-element electrode assembly depicted in FIG. 3 could be wired up with the three elements on the left side of the page connected to one wire, the middle three elements connected to a second wire, and the three elements on the right side of the page connected to a third wire. This approach is referred to herein as the "grouped element approach."

In both the independent element approach and the grouped element approach, the temperature of the hottest electrode elements in FIG. 3 can be lowered by reducing the duty cycle of the signal that drives the hottest electrode elements. More specifically, if the heat map depicted in FIG. 3 represents the resulting temperatures when all of the electrode elements are driven using the same signal, the temperatures of the three electrode elements on the left side of the page can be lowered by reducing the duty cycle of the three signals that drives those three electrode elements in the independent element approach. Similarly, when the grouped element approach is implemented, the temperatures of the three electrode elements on the left can be lowered by reducing the duty cycle of the single signal that drives those three electrode elements.

In the independent element approach, reducing the duty cycle of the signal that is applied to a given electrode element in order to reduce the temperature of that electrode element will only work if electrical isolation is maintained between the various electrode elements. For if an electrically conductive path existed between one electrode element and another electrode element, it would become impossible to apply a signal to one electrode element without applying that same signal to the other electrode element.

Similarly, in the grouped element approach, reducing the duty cycle of the signal that is applied to a given group of electrode elements in order to reduce the temperature of the electrode elements within that group will only work if electrical isolation is maintained between the various groups of electrode elements. For if an electrically conductive path existed between one group of electrode elements (e.g., the three electrode elements on the left) and another group of electrode elements (e.g., the three electrode elements on the right), it would become impossible to apply a signal to the first group of electrode elements without applying that same signal to the second group of electrode elements.

Because electrical isolation between electrode elements (or groups of electrode elements) is a prerequisite to using duty-cycle based techniques to lower the temperature of any given electrode element (or group of electrode elements), the duty-cycle based techniques described in this section cannot be combined with the FIG. 2A/B embodiment described above, which relies on a single sheet of conductive anisotropic material (e.g., the graphite sheet 70) to spread the heat away from the hottest electrode elements. This is because each of the electrode elements E1-E4 in FIG. 2A/B is electrically connected to the same sheet of graphite 70 via a respective layer of conductive material 380. Graphite has a very high electrical conductivity, so the sheet of graphite 70 in the FIG. 2A/B embodiment destroys the electrical isolation between the various electrode elements (or groups of electrode elements). And because electrical isolation must be maintained for the duty-cycle based techniques to work properly, those techniques are incompatible with the FIG. 2A/B embodiment.

Figure 4A:
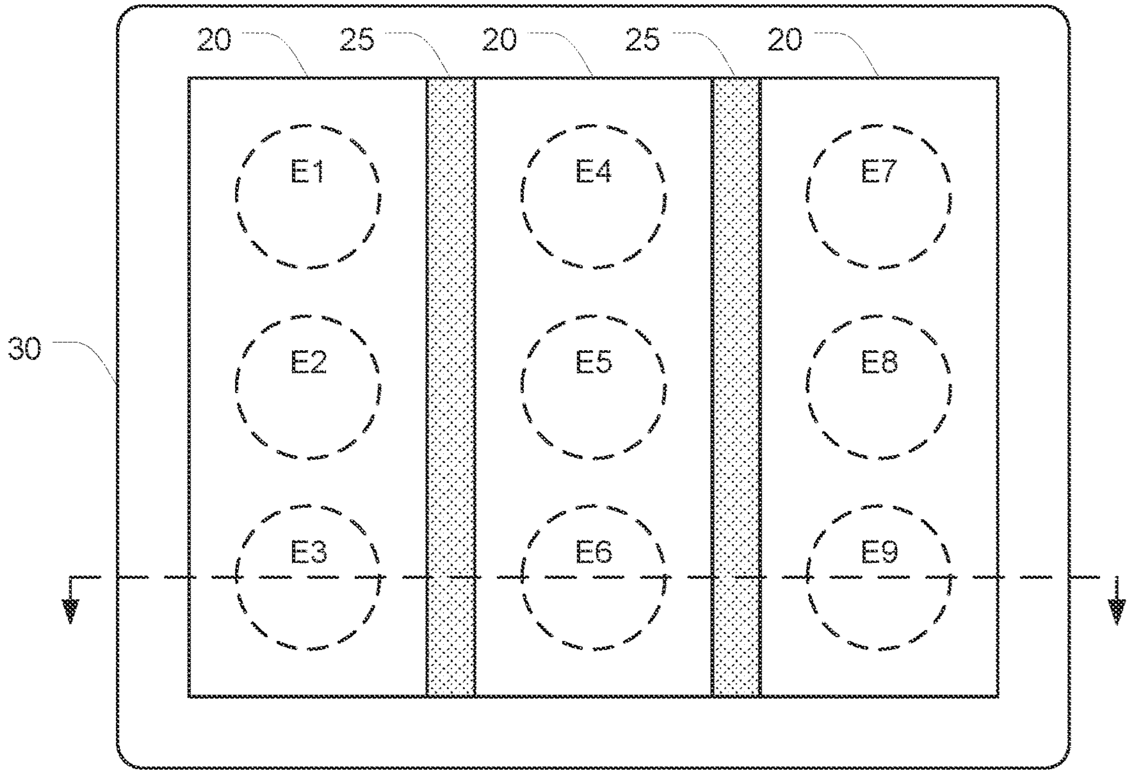
FIGS. 4A and 4B are plan and cross-section views of an illustrative electrode assembly.
Figure 4B:
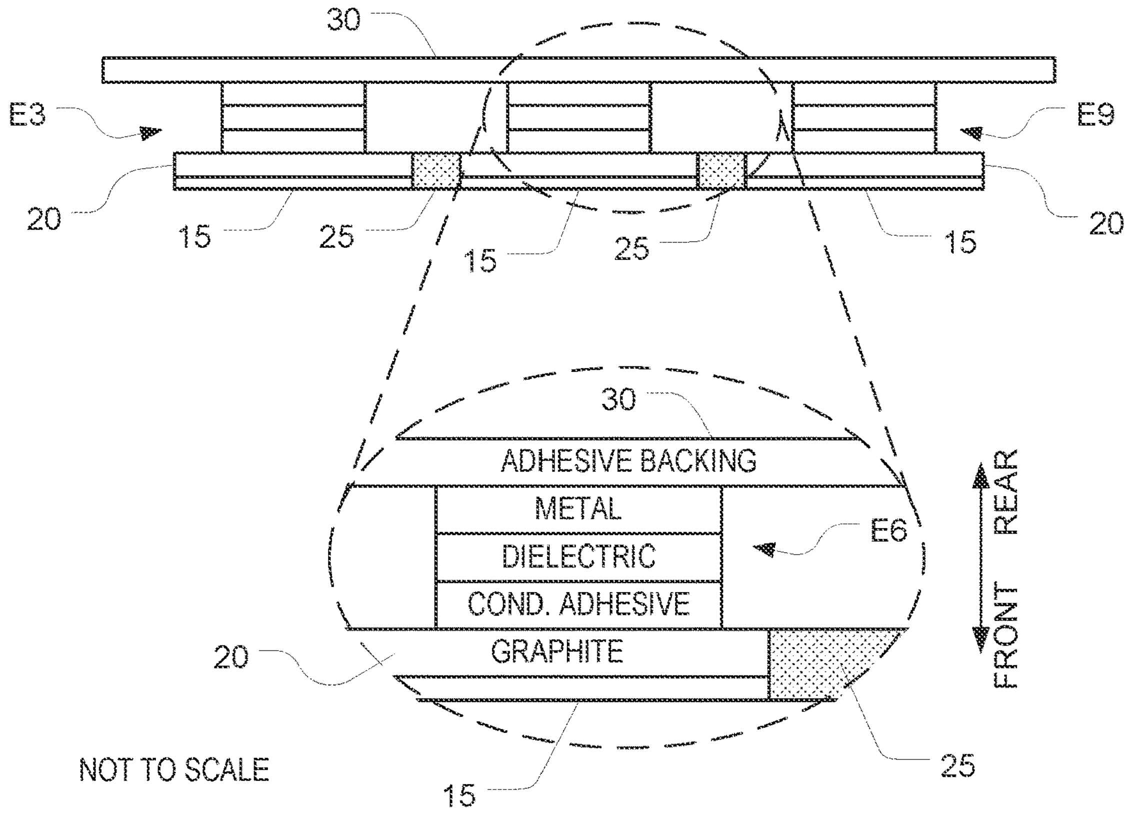

FIGS. 4A and 4B are plan and cross-sectional views of the mechanical layout of an embodiment of an electrode assembly that advantageously allows duty-cycle based techniques for reducing the temperature of certain electrode elements to coexist with conductive anisotropic material sheet (e.g., graphite-sheet) based passive heat spreading techniques. This embodiment has a plurality of sheets of conductive anisotropic material (e.g., graphite sheets 20), each of which has a front surface and a rear surface. (As used herein, the front surface faces towards the subject's body and the rear surface faces away from the subject's body.) Note that while FIG. 4A depicts three graphite sheets 20, the number of graphite sheets could vary, e.g., from 2-20. Examples of suitable forms of graphite for making the graphite sheets 20 include some types of synthetic graphite, including pyrolytic graphite, graphitized polymer film, and graphite foil made from compressed high purity exfoliated mineral graphite. Note also that while FIG. 4A depicts graphite sheets 20 that are oriented vertically, the graphite sheets 20 could also be oriented horizontally. Note that in the examples described herein and in the figures, the sheets of conductive anisotropic material are described and depicted as sheets of graphite. But in alternative embodiments, conductive anisotropic materials other than graphite may be used instead of graphite.

A plurality of electrode elements is disposed in electrical contact with each of the graphite sheets 20. In the illustrated embodiment, each of the first electrode elements (E1-E3) is disposed in electrical contact with a first graphite sheet 20 (i.e., the sheet on the left in FIG. 4A); each of the second electrode elements (E4-E6) is disposed in electrical contact with a second graphite sheet 20 (i.e., the sheet in the middle in FIG. 4A); and each of the third electrode elements (E7-E9) is disposed in electrical contact with a third graphite sheet 20 (i.e., the sheet on the right in FIG. 4A). Note that while FIG. 4A depicts three electrode elements disposed in contact with each of the graphite sheets 20, the number of electrode elements associated with each graphite sheet could vary, e.g., from 1-10. Of course, when the number of electrode elements associated with each graphite sheet is 1, only a single electrode element (as opposed to a plurality of electrode elements) will be disposed in electrical contact with each of the graphite sheets 20.

The second graphite sheet 20 is positioned adjacent to the first graphite sheet 20 without touching the first graphite sheet. When more than two graphite sheets 20 are included, the graphite sheets should be positioned adjacent to each other without touching each other. For example, in the FIG. 4A embodiment, the third graphite sheet is positioned adjacent to the second graphite sheet 20 without touching the second graphite sheet 20 and without touching the first graphite sheet 20.

A first strip 25 of electrically insulating and thermally conductive material is disposed between the first graphite sheet 20 and the second graphite sheet 20, and this first strip of material is positioned in thermal contact with both the first graphite sheet 20 and the second graphite sheet 20. When more than two graphite sheets 20 are included, additional strips of electrically insulating and thermally conductive material should be disposed between the graphite sheets. For example, in the FIG. 4A/B embodiment, a second strip 25 of electrically insulating and thermally conductive material is disposed between the second graphite sheet 20 and the third graphite sheet 20, and this second strip of material 25 is positioned in thermal contact with both the second graphite sheet and the third graphite sheet.

The purpose of these electrically insulating and thermally conductive strips of material 25 is to spread the heat away from whichever graphite sheet 20 is hottest into the neighboring graphite sheets, and thereby reduce the temperature of the hottest point on the overall electrode assembly. Notably, unlike the situation in FIG. 2A/B (where none of the electrode elements are electrically isolated from each other), the strips of material 25 are electrically insulating, and therefore provide electrical isolation between adjacent graphite sheets 20. As a result, the electrode elements E1-E9 in this FIG. 4A/B embodiment are not all electrically connected to the same sheet of graphite 70. Accordingly, electricity cannot flow from one graphite sheet 20 to another graphite sheet 20, which means that different signals can be applied to different groups of electrode elements.

In some preferred embodiments, each of the strips of material 25 comprises coated graphite. The coating may be, but is not necessarily, a tape, such as acrylic tape, polyester (polyethylene terephthalate, PET) tape, high resistant polyether ether ketone (PEEK) tape, polyimide tape, etc. But in alternative embodiments, the strips of material 25 could be made of other materials including but not limited to hexagonal boron nitride, coated (as above) isolated metal sheet, thermally conductive metal oxides, or diamond. In some preferred embodiments, each of the strips of material 25 is less than 2 mm wide. But in alternative embodiments, the strips of material 25 can be wider (e.g., 2-5 mm wide).

The FIG. 4A/B embodiment also includes a layer of skin-compatible conductive material 15 disposed on the front side of each of the graphite sheets. In some embodiments, including the embodiment illustrated in FIG. 4A/B, the layer of skin-compatible conductive material 15 is disposed on the front surface of each of the graphite sheets 20. Examples of suitable skin-compatible conductive materials include hydrogel, conductive grease, and conductive carbon filler based acrylic adhesives such as the OMNI-WAVE adhesive compositions manufactured and sold by FLEXCON (Spencer, MA, USA), and ARcare® 8006 electrically conductive adhesive composition manufactured and sold by Adhesives Research, Inc. (Glen Rock, PA, USA). During use, the front face of the conductive material 15 will be held in contact with the user's skin. Although the skin-compatible conductive material 15 can touch or partially overlap the electrically insulating strips of material 25, care should be taken to ensure that the skin-compatible conductive material 15 does not extend over the electrically insulating strips of material 25 to an extent that would compromise the electrically insulating function of those strips of material 25.

In some embodiments, including the embodiment illustrated in FIG. 4A/B, the electrode elements E1-E9 are capacitively coupled electrode elements. In these embodiments, each of the electrode elements has a respective metal layer that accepts an AC signal and a respective dielectric layer disposed on the respective metal layer. The dielectric layer of each of the electrode elements E1-E9 is disposed in electrical contact with and located behind a respective graphite sheet 20. For example, in the embodiment illustrated in FIG. 4A/B, each of the electrode elements E1-E3 has a dielectric layer that is disposed in electrical contact with and located behind the first graphite sheet 20 (i.e., the sheet on the left); each of the electrode elements E4-E6 has a dielectric layer that is disposed in electrical contact with and located behind the second graphite sheet 20 (i.e., the sheet in the middle); and each of the electrode elements E7-E9 has a dielectric layer that is disposed in electrical contact with and located behind the third graphite sheet 20 (i.e., the sheet on the right).

The dielectric layer in these embodiments could be, for example, a flat piece of ceramic material with a high dielectric constant, or a polymer layer that has a dielectric constant of at least 10, or any of the dielectric materials described above in connection with FIG. 2A/B. In these embodiments, the electrical contact between the dielectric layer of each of the electrode elements E1-E9 and the respective graphite sheet 20 is implemented using a layer of conductive adhesive. But in alternative embodiments, the electrical contact between the dielectric layer of each of the electrode elements E1-E9 and the respective graphite sheet 20 can be implemented using another approach (e.g., a layer of conductive gel, such as a hydrogel), e.g., using any of the approaches described above in connection with FIG. 2A/B.

The FIG. 4A/B embodiment also includes a support 30 having an adhesive backing. This support can be made, for example, from a fabric or a foam material (e.g., similar to a conventional self-adhesive bandage). The support 30 is shaped and dimensioned to hold the electrode assembly against a person's body with the graphite sheets facing the person's body.

The electrical connections to the electrode elements E1-E9 in the FIG. 4A/B embodiment may be implemented using a variety of approaches, including the independent element approach and the grouped element approach described above.

Figure 5:
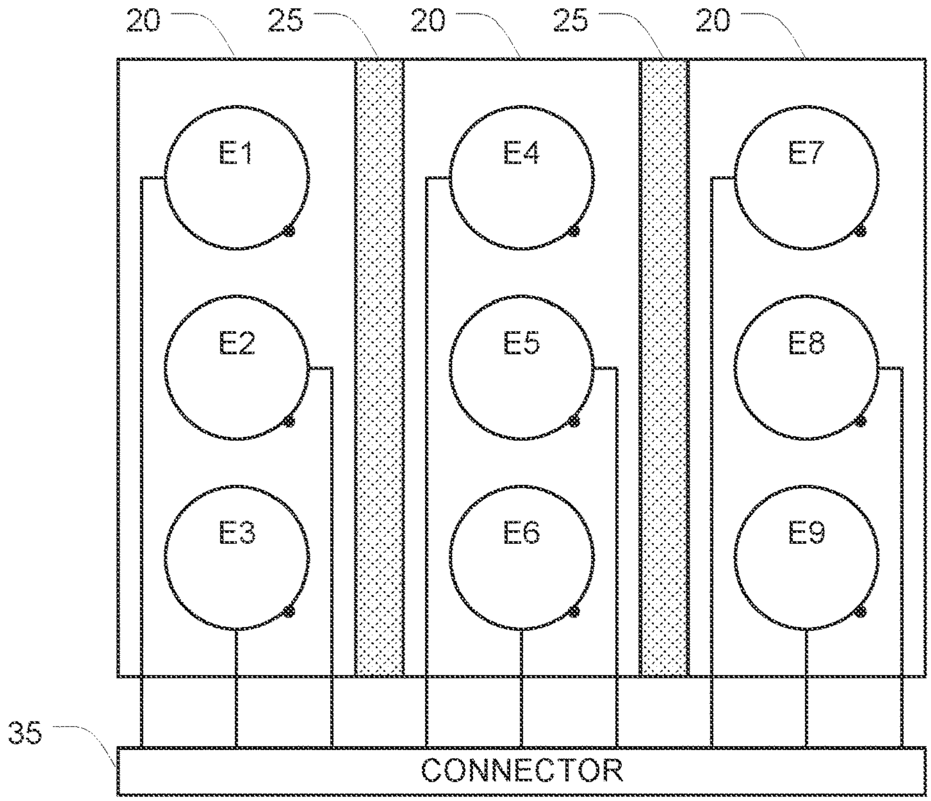
FIG. 5 depicts one suitable set of electrical connections to the electrode elements in the FIG. 4A/B embodiment.

FIG. 5 shows a suitable set of electrical connections to the electrode elements E1-E9 for implementing the independent element approach when each of the electrode elements E1-E9 includes a metal layer and a dielectric layer (as shown in FIG. 4A/B). The heavy dot in the lower right quadrant of each electrode element E1-E9 represents the electrical contact between the dielectric layer of each of the electrode elements E1-E9 and the respective graphite sheet 20. Any of the forms of graphite described above in connection with FIG. 4A/B may be used in this FIG. 5 embodiment, or non-graphite conductive anisotropic materials may be used. An individual metal conductor (e.g., one or more wires and/or conductive traces) runs from the metal layer of each of the electrode elements E1-E9 to a respective pin of the connector 35. And these metal conductors route AC signals that are applied to the connector 35 to the metal layers of each of the electrode elements E1-E9, respectively. Thus, each individual electrode element can be activated independently using an independent wire. Note, however, that this independence is compromised within the confines of any single one of the graphite sheets 20 because each graphite sheet 20 conducts electricity.

When the wiring configuration depicted in FIG. 5 is used, the problematic situation depicted in FIG. 3 (in which the three elements on the left run hotter than the remaining electrode elements) can be ameliorated by reducing the duty cycle of the signals that are applied to the three electrode elements on the left (i.e., electrode elements E1-E3 in FIGS. 4 and 5), thereby reducing the temperature of those three electrode elements. Notably, because each of the graphite sheets 20 is thermally conductive, each graphite sheet will also operate to passively spread the heat away from the hottest electrode elements within any given sheet. And in addition, because the strips of material 25 are thermally conductive, the passive spreading of heat is not limited to the confines of any given single graphite sheet. To the contrary—whichever graphite sheet 20 is the hottest can dissipate some of its heat into the neighboring graphite sheets via the thermally conductive strips of material 25. This FIG. 4/5 embodiment therefore advantageously combines both duty-cycle based techniques for reducing temperature compatible with passive heat spreading techniques for reducing temperature.

As noted above, because each graphite sheet 20 conducts electricity, the independence of all the electrode elements within any given graphite sheet 20 is compromised. In view of this, a result that is very similar to the result described above in connection with FIG. 5 can be achieved by wiring all of the electrode elements that sit on any given graphite sheet 20 together in parallel, as depicted in FIG. 6.

Figure 6:
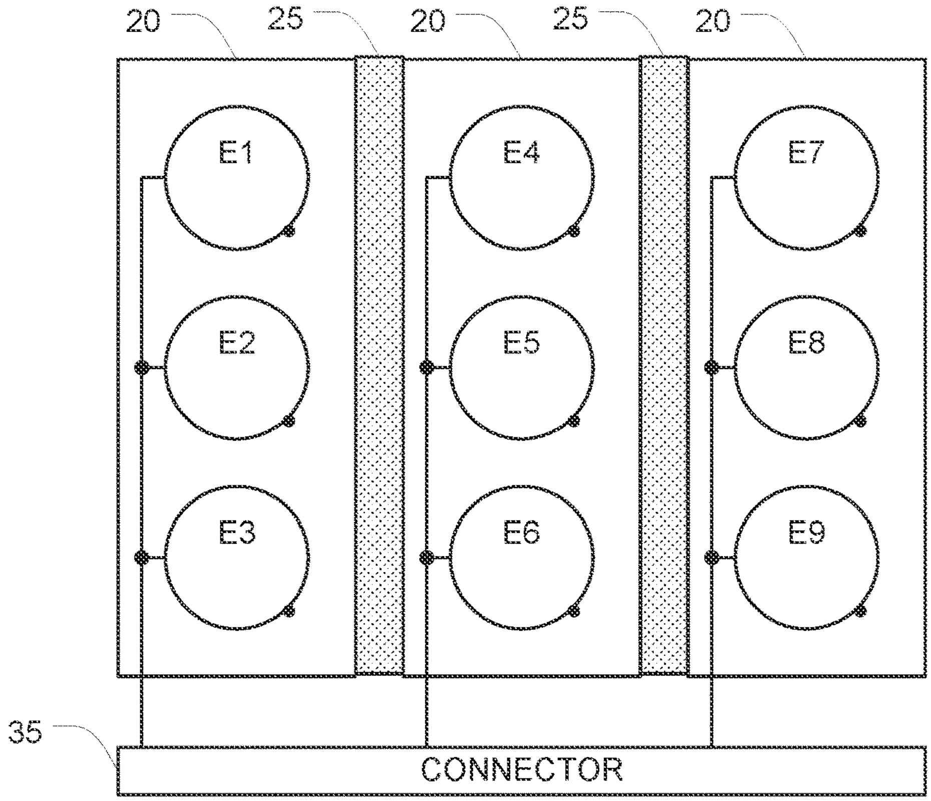
FIG. 6 shows an alternative suitable set of electrical connections to the electrode elements in the FIG. 4A/B embodiment.

FIG. 6 shows an alternative suitable set of electrical connections to the electrode elements E1-E9 for implementing the grouped element approach when each of the electrode elements E1-E9 includes a metal layer and a dielectric layer (as shown in FIG. 4A/B). The heavy dot in the lower right quadrant of each electrode element E1-E9 represents the electrical contact between the dielectric layer of each of the electrode elements E1-E9 and the respective graphite sheet 20. Any of the forms of graphite described above in connection with FIG. 4A/B may be used in this FIG. 6 embodiment, or non-graphite conductive anisotropic materials may be used. One set of metal conductors (e.g., wires or conductive traces) runs from the metal layer of all three electrode elements E1-E3 to one pin of the connector 35. Another set of metal conductors runs from the metal layer of all three of the electrode elements E4-E6 to another pin of the connector 35. And yet another set of metal conductors runs from the metal layer of all three of the electrode elements E7-E9 to yet another pin of the connector 35. Each set of metal conductors routes AC signals that are applied to the connector 35 to the metal layers of each group of electrode elements, respectively (i.e., E1-E3, E4-E6, or E7-E9, respectively). Thus, each group of electrode elements can be activated independently from the other groups using an independent wire.

The wiring configuration depicted in FIG. 6 is therefore another approach for ameliorating the problematic situation depicted in FIG. 3 (in which the three elements on the left run hotter than the remaining electrode elements) by reducing the duty cycle of the signals that are applied to those three electrode elements. Here again, because each of the graphite sheets 20 is thermally conductive, each graphite sheet will also operate to passively spread the heat away from the hottest electrode elements within any given sheet. Whichever graphite sheet 20 is the hottest can also dissipate some of its heat into the neighboring graphite sheets via the thermally conductive strips of material 25. This FIG. 4/6 embodiment therefore also advantageously combines both duty-cycle based techniques for reducing temperature with passive heat spreading techniques for reducing temperature.

Yet another approach for making electrical connections to the electrode elements E1-E9 is to distribute the electrode elements E1-E9 on to different graphite sheets (e.g., as described above in connection with FIG. 6), but wire all the electrode elements E1-E9 in parallel. When this approach is employed, only a single electrical connection to the connector is needed to energize all nine elements.

The embodiments described above in connection with FIG. 4-6 assume that each of the electrode elements E1-E9 is a capacitively coupled electrode element that includes a layer of metal positioned behind a dielectric layer. But the scope of this application is not limited to capacitively coupled electrode elements. To the contrary, electrode elements that are not capacitively coupled may be employed.

Figure 7A:
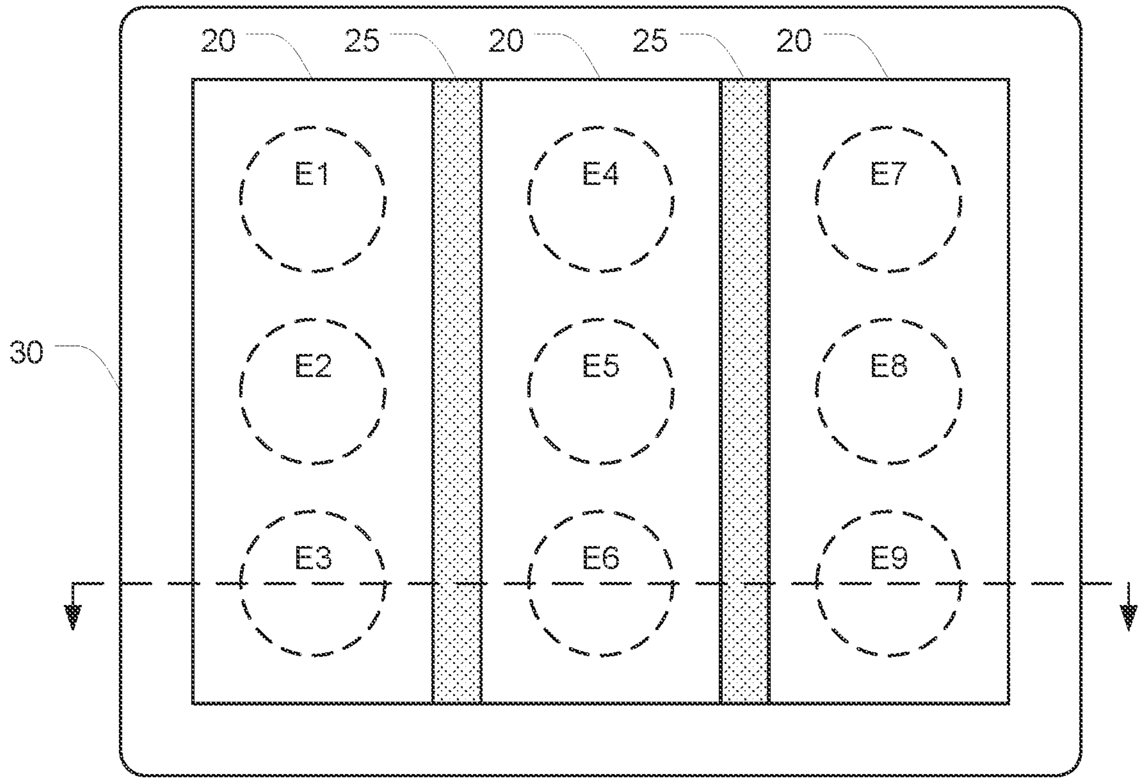
FIGS. 7A and 7B are plan and cross-sectional views of another illustrative electrode assembly.
Figure 7B:
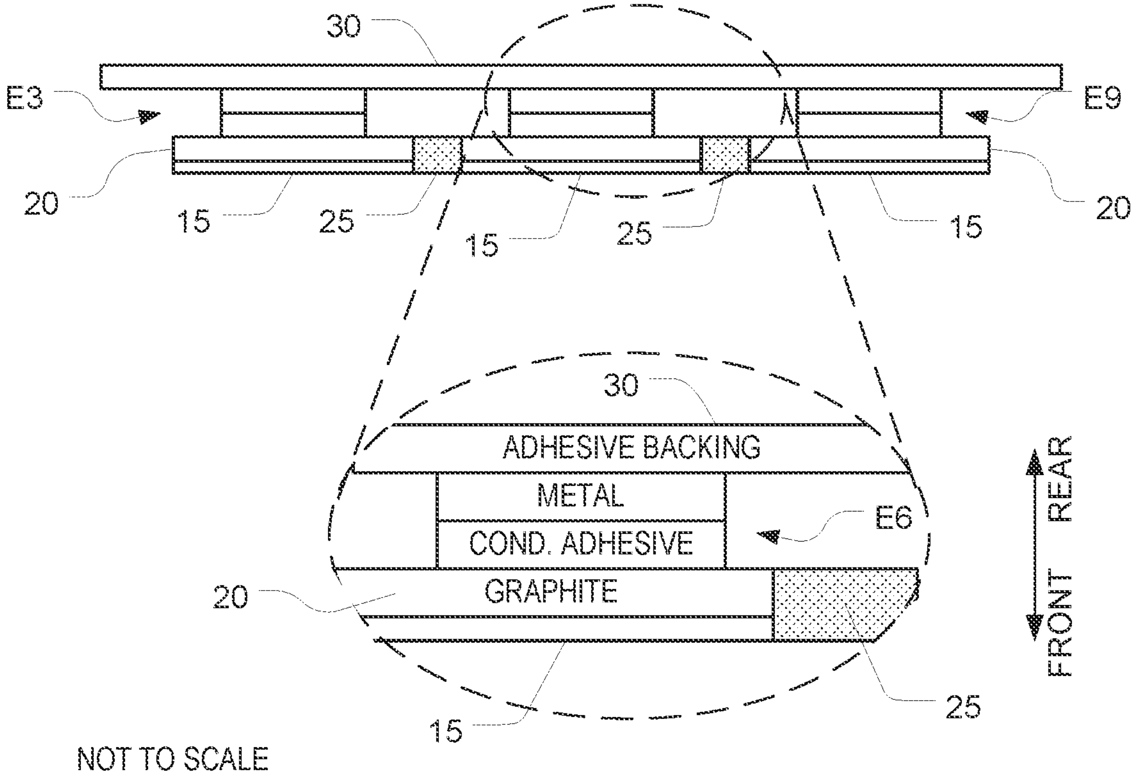

FIGS. 7A and 7B are plan and cross-sectional views of the mechanical layout of another embodiment of an electrode assembly that advantageously allows duty-cycle based techniques for reducing the temperature of certain electrode elements to coexist with conductive anisotropic material sheet (e.g., graphite-sheet) based passive heat spreading techniques. This embodiment also has a plurality of sheets of conductive anisotropic material (e.g., graphite sheets 20), each of which has a front surface and a rear surface. Note that while FIG. 7A depicts three graphite sheets 20, the number of graphite sheets could vary, e.g., from 2-20. The forms of graphite described above in connection with FIG. 4A/B may be used in this FIG. 7A/B embodiment, or other conductive anisotropic materials may be used instead of graphite.

A plurality of electrode elements E1-E9 is disposed in electrical contact with each of the graphite sheets 20. For example, in the illustrated embodiment, each of the first electrode elements (E1-E3) is disposed in electrical contact with a first graphite sheet 20 (i.e., the sheet on the left in FIG. 7A); each of the second electrode elements (E4-E6) is disposed in electrical contact with a second graphite sheet 20 (i.e., the sheet in the middle in FIG. 7A); and each of the third electrode elements (E7-E9) is disposed in electrical contact with a third graphite sheet 20 (i.e., the sheet on the right in FIG. 7A). Note that while FIG. 7A depicts three electrode elements disposed in contact with each of the graphite sheets 20, the number of electrode elements associated with each graphite sheet could vary, e.g., from 1-10. Of course, when the number of electrode elements associated with each graphite sheet is 1, only a single electrode element (as opposed to a plurality of electrode elements) will be disposed in electrical contact with each of the graphite sheets 20.

The second graphite sheet 20 is positioned adjacent to the first graphite sheet 20 without touching the first graphite sheet. When more than two graphite sheets 20 are included, the graphite sheets should be positioned adjacent to each other without touching each other, as described above in connection with the FIG. 4A/B embodiment.

One or more strips 25 of electrically insulating and thermally conductive material are disposed between the graphite sheets 20, as described above in connection with the FIG. 4A/B embodiment. The purpose of these electrically insulating and thermally conductive strips of material 25 is to spread the heat away from whichever graphite sheet 20 is hottest into the neighboring graphite sheets, and thereby reduce the temperature of the hottest point on the overall electrode assembly. Notably, unlike the situation in FIG. 2A/B (where none of the electrode elements are electrically isolated from each other), the strips of material 25 are electrically insulating, and therefore provide electrical isolation between adjacent graphite sheets 20. As a result, the electrode elements E1-E9 in this FIG. 7A/B embodiment are not all electrically connected to the same sheet of graphite 70. Accordingly, electricity cannot flow from one graphite sheet 20 to another graphite sheet 20, which means that different signals can be applied to different groups of electrode elements.

The FIG. 7A/B embodiment also includes a layer of skin-compatible conductive material 15 disposed on the front side of each of the graphite sheets (e.g., as shown, on the front surface of each of the graphite sheets), as described above in connection with the FIG. 4A/B embodiment.

Notably, unlike the FIG. 4A/B embodiment, in which each electrode element E1-E9 includes a layer of metal positioned behind a dielectric layer that is in turn disposed in electrical contact with a respective sheet of graphite, the electrode elements E1-E9 in this FIG. 7A/B embodiment do not include dielectric layers. Instead, the electrode elements E1-E9 in the FIG. 7A/B embodiment have a metal layer that is disposed in electrical contact with a respective sheet of graphite 20, without an intervening dielectric layer. For example, in the embodiment illustrated in FIG. 7A/B, each of the electrode elements E1-E3 has a metal layer that is disposed in electrical contact with and located behind the first graphite sheet 20 (i.e., the sheet on the left); each of the electrode elements E4-E6 has a metal layer that is disposed in electrical contact with and located behind the second graphite sheet 20 (i.e., the sheet in the middle); and each of the electrode elements E7-E9 has a metal layer that is disposed in electrical contact with and located behind the third graphite sheet 20 (i.e., the sheet on the right).

In the illustrated embodiment, the electrical contact between the metal layer of each of the electrode elements E1-E9 and the respective graphite sheet 20 is implemented using a layer of conductive adhesive. But in alternative embodiments, the electrical contact between the metal layer of each of the electrode elements E1-E9 and the respective graphite sheet 20 can be implemented using another approach (e.g., a layer of conductive gel, such as a hydrogel).

The FIG. 7A/B embodiment also includes a support 30 having an adhesive backing that is similar to the support 30 described above in connection with the FIG. 4A/B embodiment.

The electrical connections to the electrode elements E1-E9 in the FIG. 7A/B embodiment may be implemented using a variety of approaches, including the independent element approach and the grouped element approach, and the approaches for making the electrical connections described above in connection with FIG. 5-6 may be used for the FIG. 7A/B embodiment (except that the electrical connections with the graphite sheets are made to the metal layer of each electrode element E1-E9 instead of to the dielectric layer).

Figure 8:
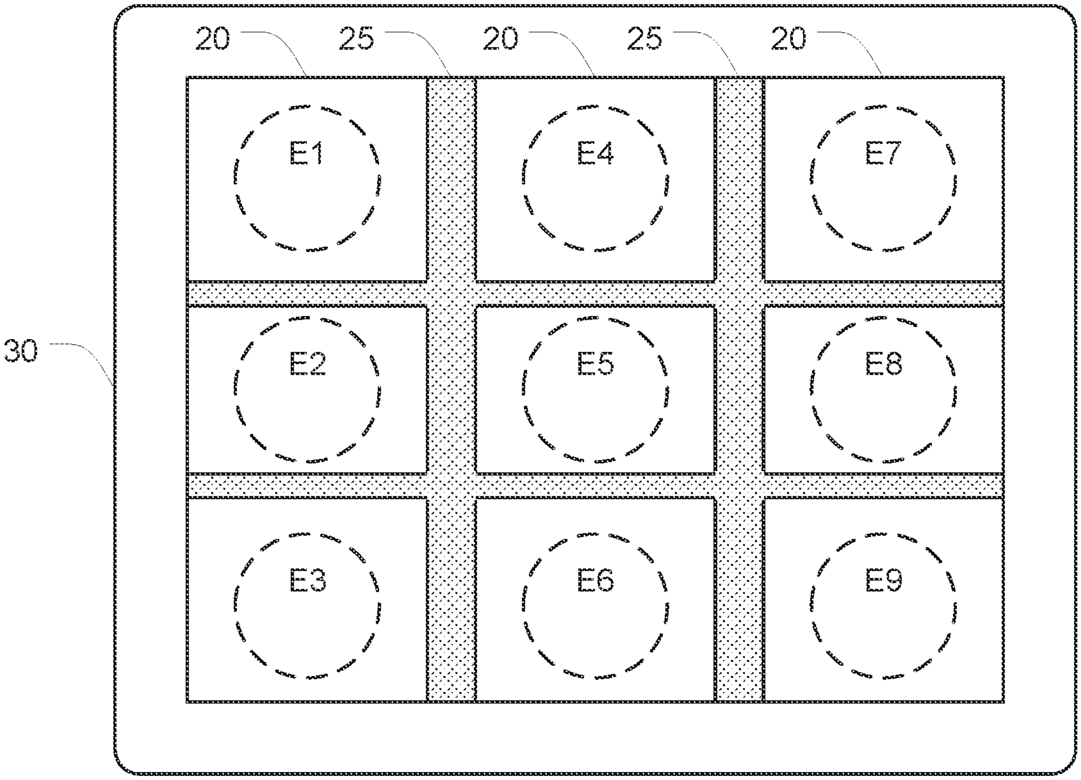
FIG. 8 depicts another electrode assembly in which the number of graphite sheets matches the number of electrode elements.

In the embodiments depicted in FIGS. 4-7, a plurality of electrode elements is disposed in electrical contact with each graphite sheet. But in alternative embodiments, the number of sheets of conductive anisotropic material (e.g., graphite sheets) may be increased to match the number of electrode elements, in which case only a single electrode element is disposed in electrical contact with any given sheet of conductive anisotropic material (e.g., graphite sheet), as depicted in FIG. 8. In still other embodiments (not shown), a plurality of electrode elements are disposed in electrical contact with some of the sheets of conductive anisotropic material, and only a single electrode element is disposed in electrical contact with each of the remaining sheets of conductive anisotropic material. The forms of graphite described above in connection with FIG. 4A/B may be used in these embodiments, or other conductive anisotropic materials may be used instead of graphite.

The FIG. 8 embodiment and the alternatives described in the previous paragraph may be implemented using electrode elements that are capacitively coupled, or using electrode elements that are not capacitively coupled. When the electrode elements are capacitively coupled, the electrical connection between any given electrode element E1-E9 and the respective graphite sheet 20 will be made between the dielectric layer of the electrode element E1-E9 and the respective graphite sheet 20 (e.g., as described above in connection with FIG. 4A/B). Alternatively, when the electrode elements are not capacitively coupled, the electrical connection between any given electrode element E1-E9 and the respective graphite sheet 20 will be made between the metal layer of the electrode element E1-E9 and the respective graphite sheet 20 (e.g., as described above in connection with FIG. 7A/B).

In this FIG. 8 embodiment, strips of electrically insulating and thermally conductive material 25 are disposed between the graphite sheets 20. The construction and shape of these strips of material 25 can be as described above in connection with FIG. 4A/B, and these strips of material 25 are positioned in thermal contact with any adjacent graphite sheets 20. The purpose of these electrically insulating and thermally conductive strips of material 25 is to spread the heat away from whichever graphite sheet 20 is hottest into the neighboring graphite sheets, and thereby reduce the temperature of the hottest point on the overall electrode assembly. Notably, these strips of material 25 are electrically insulating, and therefore provide electrical isolation between adjacent graphite sheets 20. As a result, the electrode elements E1-E9 in this FIG. 8 embodiment are all electrically isolated from each other. Accordingly, electricity cannot flow from one graphite sheet 20 to another graphite sheet 20, which means that different signals can be applied to each individual electrode element. As described above, the electrode assembly may be secured in place against a person's body using an adhesive backing that is similar to the support 30 described above in connection with the FIG. 4A/B and FIG. 7A/B embodiments.

When the electrode assemblies are constructed as depicted in FIG. 8, and a plurality of electrode assemblies are positioned on opposite sides of a target region, the electrode assemblies can be used to perform impedance tomography of the target region in an apparatus designed both for performing electrical impedance tomography (EIT) and for treating a condition with TTFields treatment featuring temperature control of the array. The use of transducer arrays to perform EIT has been described in U.S. patent application Ser. No. 17/710,041 (filed Mar. 31, 2022), which is hereby incorporated by reference in the present disclosure.

For example, if each electrode assembly includes N electrode elements (where N is at least 4), this may be accomplished by using appropriate switching circuitry and impedance measurement circuitry to sequentially measure the impedances between each of the N electrode elements positioned on one side of the target region and each of the N electrode elements positioned on the other side of the target region, resulting in a total of N 2 impedance measurements. These impedance measurements are then fed into a back propagation algorithm to generate an impedance map of the space that lies between the electrode assemblies. This impedance map, or a series of such maps taken over a period of time, may subsequently be used to develop a treatment plan, modify a previously developed treatment plan, or monitor progression (growth) or regression (shrinkage) of one or more cancers, tumors or metastases during the course of an extended TTFields treatment, and alter the positioning of the transducer arrays in response thereto.

In some embodiments, only a subset of the electrode elements that have been placed on the subject's body are used in the impedance measurements. For example, if a pair of 5×5 arrays of electrode elements are placed on the subject body on opposite sides of a target region, the switching circuitry and impedance measurement circuitry can be used to sequentially measure the impedances between each of N=16 electrode elements positioned on one side of the target region and each of M=21 electrode elements positioned on the other side of the target region, resulting in a total of N×M (i.e., 336) impedance measurements. These impedance measurements are then fed into the back propagation algorithm to generate the impedance map of the space that lies between the N electrode elements and the M electrode elements.

After the treatment plan is generated, an alternating voltage is applied between a majority (or at least a plurality) of the electrode elements on one side of the target region and a majority (or at least a plurality) of the electrode elements on the other side of the target region, which will induce an alternating electric field in the target region.

In the embodiments described above in connection with FIGS. 4-8, all of the sheets of conductive anisotropic material 20 (e.g., graphite sheets) in any given embodiment are roughly the same size, and each of those sheets of conductive anisotropic material 20 makes contact with the same number of electrode elements (e.g., three electrode elements in FIG. 4-7, or a single electrode element in FIG. 8). But in alternative embodiments (not shown), the size of the sheets of conductive anisotropic material 20 can vary within a single electrode assembly and/or the number of electrode elements that contact any given sheet of conductive anisotropic material 20 can vary. For example, some sheets of conductive anisotropic material 20 can make contact with only a single electrode element, while other sheets of conductive anisotropic material 20 can make contact with two or more electrode elements. In another example, some sheets of conductive anisotropic material 20 can make contact with two electrode elements, while other sheets of conductive anisotropic material 20 can make contact with three or more electrode elements.

Headings are provided for convenience only and are not to be construed to limit the invention in any manner. Embodiments illustrated under any heading or in any portion of the disclosure may be combined with embodiments illustrated under the same or any other heading or other portion of the disclosure.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An electrode assembly comprising:

a first sheet of a conductive anisotropic material having a front side and a front surface and a rear side and a rear surface;

one or more first electrode elements, each of which is disposed in electrical contact with the first sheet;

a second sheet of conductive anisotropic material having a front side and a front surface and a rear side and a rear surface, wherein the second sheet is positioned adjacent to the first sheet without touching the first sheet;

one or more second electrode elements, each of which is disposed in electrical contact with the second sheet; and a first strip of electrically insulating and thermally conductive material disposed between the first sheet and the second sheet, wherein the first strip of material is positioned in thermal contact with both the first sheet and the second sheet.

2. The electrode assembly of claim 1, wherein the first strip of material comprises coated graphite.

3. The electrode assembly of claim 1, wherein the first strip of material is less than 2 mm wide.

4. The electrode assembly of claim 1, wherein the first sheet comprises a sheet of synthetic graphite, pyrolytic graphite, graphitized polymer film, or graphite foil made from compressed high purity exfoliated mineral graphite, and wherein the second sheet comprises a sheet of synthetic graphite, pyrolytic graphite, graphitized polymer film, or graphite foil made from compressed high purity exfoliated mineral graphite.

5. The electrode assembly of claim 1, further comprising:

a first layer of skin-compatible conductive material disposed on the front side of the first sheet; and a second layer of skin-compatible conductive material disposed on the front side of the second sheet.

6. The electrode assembly of claim 1, wherein there are at least two first electrode elements, wherein each of the first electrode elements comprises a respective first metal layer and a respective first dielectric layer disposed on the respective first metal layer, and wherein each of the first dielectric layers is disposed in electrical contact with and located behind the first sheet, and wherein there are at least two second electrode elements, wherein each of the second electrode elements comprises a respective second metal layer and a respective second dielectric layer disposed on the respective second metal layer, and wherein each of the second dielectric layers is disposed in electrical contact with and located behind the second sheet.

7. The electrode assembly of claim 6, wherein each of the first dielectric layers and each of the second dielectric layers comprises a polymer layer having a dielectric constant of at least 10.

8. The electrode assembly of claim 6, wherein the electrical contact between each of the first dielectric layers and the first sheet is implemented using a first layer of conductive gel or conductive adhesive, and wherein the electrical contact between each of the second dielectric layers and the second sheet is implemented using a second layer of conductive gel or conductive adhesive.

9. The electrode assembly of claim 1, wherein there are at least two first electrode elements, and wherein each of the first electrode elements comprises a respective first metal layer disposed in electrical contact with the first sheet, and wherein there are at least two second electrode elements, and wherein each of the second electrode elements comprises a respective second metal layer disposed in electrical contact with the second sheet.

10. The electrode assembly of claim 1, wherein there are at least two first electrode elements and at least two second electrode elements, and wherein the electrode assembly further comprises:

a plurality of first metal conductors, each of which is disposed in electrical contact with only a single respective one of the first electrode elements; and a plurality of second metal conductors, each of which is disposed in electrical contact with only a single respective one of the second electrode elements.

11. The electrode assembly of claim 1, wherein there are at least two first electrode elements and at least two second electrode elements, and wherein the electrode assembly further comprises:

at least one first metal conductor arranged to electrically connect all of the first electrode elements; and at least one second metal conductor arranged to electrically connect all of the second electrode elements.

12. The electrode assembly of claim 1, further comprising a coil, wherein energy from a main conductor power source is diverted by the coil and stored locally on a capacitor for reuse in powering a controller, or a circuit, or a means to generate digital data related to temperature measurements.

13. The electrode assembly of claim 1, wherein there are at least two first electrode elements and at least two second electrode elements, and wherein the electrode assembly further comprises:

a third sheet of a conductive anisotropic material having a front side and a front surface and a rear side and a rear surface, wherein the third sheet is positioned adjacent to the second sheet without touching the second sheet and without touching the first sheet;

a plurality of third electrode elements, each of which is disposed in electrical contact with the third sheet; and a second strip of electrically insulating and thermally conductive material disposed between the second sheet and the third sheet, wherein the second strip of material is positioned in thermal contact with both the second sheet and the third sheet.

14. The electrode assembly of claim 13, further comprising:

a plurality of first metal conductors, each of which is disposed in electrical contact with only a single respective one of the first electrode elements;

a plurality of second metal conductors, each of which is disposed in electrical contact with only a single respective one of the second electrode elements; and a plurality of third metal conductors, each of which is disposed in electrical contact with only a single respective one of the third electrode elements.

15. The electrode assembly of claim 13, further comprising:

a first layer of skin-compatible conductive material disposed on the front side of the first sheet;

a second layer of skin-compatible conductive material disposed on the front side of the second sheet; and a third layer of skin-compatible conductive material disposed on the front side of the third sheet, wherein the first strip of material comprises coated graphite, and wherein the second strip of material comprises coated graphite.

16. The electrode assembly of claim 1, wherein there is one first electrode element and one second electrode element, and wherein the electrode assembly further comprises:

a third sheet of a conductive anisotropic material having a front side and a front surface and a rear side and a rear surface, wherein the third sheet is positioned adjacent to the second sheet without touching the second sheet and without touching the first sheet;

one third electrode element, disposed in electrical contact with the third sheet; and a second strip of electrically insulating and thermally conductive material disposed between the second sheet and the third sheet, wherein the second strip of material is positioned in thermal contact with both the second sheet and the third sheet.

17. The electrode assembly of claim 16, wherein the first strip of material and the second strip of material each comprise coated graphite.

18. The electrode assembly of claim 16, wherein each of the first sheet, the second sheet and the third sheet comprises a sheet of synthetic graphite, pyrolytic graphite, graphitized polymer film, or graphite foil made from compressed high purity exfoliated mineral graphite.

19. The electrode assembly of claim 16, wherein there are a plurality of electrode elements, each disposed in electrical contact with a respective sheet of a plurality of sheets and each electrically isolated from each other; wherein each sheet is separated from adjacent sheets by strips of electrically insulating and thermally conductive material, and wherein each strip of electrically insulating and thermally conductive material are in thermal contact with the adjacent sheets.

20. The electrode assembly of claim 19, wherein each of the sheets comprises a sheet of synthetic graphite, pyrolytic graphite, graphitized polymer film, or graphite foil made from compressed high purity exfoliated mineral graphite.

* * * * *